United States Patent
Bader (12)

(10) Patent No.: US 6,468,792 B1
(45) Date of Patent: Oct. 22, 2002

(54) PROCESS AND DEVICE FOR CULTURING AND/OR TREATING CELLS

(76) Inventor: Augustine Bader, Hinter den Langen Hoefen 16, D-31275 Lehrte (DE)

( * ) Notice: Subject to any disclaimer, the term of this patent is extended or adjusted under 35 U.S.C. 154(b) by 0 days.

(21) Appl. No.: 09/423,699

(22) PCT Filed: May 11, 1998

(86) PCT No.: PCT/EP98/02745

§ 371 (c)(1),
(2), (4) Date: Nov. 10, 1999

(87) PCT Pub. No.: WO98/51779

PCT Pub. Date: Nov. 19, 1998

(30) Foreign Application Priority Data

May 10, 1997 (DE) .......................................... 197 19 751

(51) Int. Cl.⁷ ............................ C12M 1/00; C12M 3/00; C12N 1/00; C12N 7/00; C12N 5/00
(52) U.S. Cl. .................... 435/325; 435/235.1; 435/243; 435/283.1; 435/289.1
(58) Field of Search ................................ 435/243, 325, 435/283.1, 289.1, 235.1

(56) References Cited

U.S. PATENT DOCUMENTS 4,661,455 A    4/1987   Hubbard ..................... 435/240

FOREIGN PATENT DOCUMENTS

| EP | 0725134 A2 | 8/1996 |
| WO | WO 90/05179 | 5/1990 |
| WO | WO 96/30497 | 10/1996 |

*Primary Examiner*—David M. Naff
*Assistant Examiner*—Deborah K. Ware
(74) *Attorney, Agent, or Firm*—Cook, Alex, McFarron, Manzo, Cummings & Mehler

(57) ABSTRACT

A device and method for culturing and/or treating cells is provided. The device comprises a first cell chamber on a gas-permeable carrier and has at least one supply and/or discharge line as well as a frame. The cell chamber is formed by a first film that is gas-permeable and a second film which is microporous that is arranged or is integral with the first film. The frame of the device is useful for covering the films. Also at least one of the first and second films is elastic so that a final volume of the cell chamber can expand to at least 100 times its starting volume. This allows for flexibility of the cell chamber into which cells are introduced therein, and the chamber is between the first and second film. A third film can also be arranged on the second film of which these films being elastic form a second cell chamber having a variable volume of at least 100 times its starting volume.

16 Claims, 2 Drawing Sheets

PROCESS AND DEVICE FOR CULTURING AND/OR TREATING CELLS

BACKGROUND OF THE INVENTION

1. Field of the Invention

The invention relates to a device for culturing and/or treating cells.

2. Description of the Related Prior Art

DE 42 06 585 C2 describes a device for the mass culture of cells, in particular of hepatocytes on plate-like cell culture carriers, with cells being arranged in a collagen layer on a gas-permeable cell culture carrier. In this connection, the device is constructed like a sandwich, with several cell culture carriers being provided with intercalated collagen layers containing cells. A disadvantage of this device is that the cell chambers are always precisely defined and possess specific volumes. In addition, it is difficult to observe the cells in cell chambers in order to ascertain any possible changes or developmental states.

DE 42 22 345 A1 describes a method for culturing a cell type, in a coculture method using liver cells, with liver cells being cultured on a carrier in a sandwich method. A first matrix layer is arranged between the liver cells and the carrier for anchoring the liver cells, and a second matrix layer is situated over the liver cells.

U.S. Pat. No. 5,449,617 describes a culture vessel in which the culturing is carried out in rigid housings. A disadvantage in this connection is the high proportion of dead volume. In order to supply the cells more efficiently and more uniformly with oxygen, the appliance preferably has to be rotated. This is a continuous stress factor, particularly for cells which are growing in an adherent manner. In this connection, it is not possible to use the so-called sandwich technique to produce hepatocyte cultures over any great length of time since such rotations result in the collagen layers being destroyed. It is only possible to scale up these methods in conjunction with a high dead volume. This limits the scale-up substantially, since an increase in volume also causes the limits of the scale-up to be reached rapidly since new conditions are continually being met with. These are also determined by the fact that the tumbling action achieved by the rotation then increases the pressure and shearing stresses on the cells. On the other hand, if these rotations are not effected, it is no longer possible to ensure that the cells are supplied uniformly with oxygen. This is because of the lateral arrangement of the gas-permeable films/membranes relative to the cell culture space.

U.S. Pat. No. 4,748,124 describes the introduction of defined volumes for the chambers of the culture system. For this purpose, the culture chamber is kept in a compressed state. This suffers from the disadvantage that these chambers have to be fixed in given dimensions (defined) before starting the culturing. This definition of the culture space is regarded as being an advantage. In fact, it is a crucial disadvantage since it makes it impossible to adjust to different culture phases and also makes it impossible for the culture system to increase in size to keep pace with 3-D growth. However, it is only such flexibility which enables the system to be used for developing artificial organs from a small number of starter cultures.

In addition, U.S. Pat. No. 4,748,124 only uses dialysis membranes. This is a considerable disadvantage in the case of primary cells such as hepatocytes, which transport (have to take up and release) products and catabolites, or protein-bound toxins having a substantial, relatively high, molecular weight. Only protein-permeable microporous membranes are able to ensure this.

SUMMARY OF THE INVENTION

The present invention is based on the object of providing a device which can be used to react in a very variable manner to the changing conditions, in particular changes in volume (increase and decrease in the volume) when treating and/or culturing cells, where, at the same time an observation should also be possible and, in addition, it should also be made possible to carry out a mass culture.

Because of its simple construction, the novel device is suitable for a mass culture system. In addition, it can be adapted to the particular requirements at the time. Thus, it is possible, beginning with a very small volume and a low number of cells-which are being treated or cultured in the cell chamber or cell compartment, subsequently to increase these parameters to many times the starting volume. This means, for example, that it is possible to start with a small quantity of the material to be investigated and then to allow this material to grow in the cell chamber. This also achieves a saving in costs, particularly in the case of expensive substances.

Because of the possibility of supplying, by way of the stable carrier, air or oxygen which is able to diffuse through the gas-permeable films into the cell chamber, one or more such units can be placed, one above the other in the form of a sandwich, in a conventional incubator. As a result of combining the carrier structure and the oxygenation through the gas-permeable films, there is no need at all for pumping devices for supplying the oxygen and the carbon dioxide, thereby facilitating the operation of the device.

A further advantage is also the fact that, in the novel device, the cell chamber can always be observed in a simple manner.

While cells can be treated or cultured in the lower cell chamber, the upper chamber can be earmarked for supplying nutrient medium, which diffuses into the cell chamber through the microporous film or membrane. For this, the second film has to be appropriately microporous and liquid-permeable. A further advantage of supplying nutrient medium in this way is that the cells in the cell chamber are then subjected to substantially less shearing stress. The cells can be embedded in collagen, both above and below, with nutrient medium then being supplied from above.

Another option for using the second chamber is that this chamber can also be used for producing or "harvesting" substances which are formed in the cell chamber. Thus, white blood cells, for example, can be cultured in the cell chamber and exposed to an antigen, resulting in the cells beginning to produce antibodies. These antibodies then diffuse through the second film into the second chamber and can then be withdrawn from this chamber. In this way, the cells are retained in the cell chamber. In this case, it is only necessary to ensure that the second film between the cell chamber and the second chamber possesses an appropriate microporosity, such that only the desired substances are able to perfuse through the film.

It is furthermore also advantageous that the medium which is present in the second chamber can be exchanged without disturbing the cells which are present in the cell chamber. Of course, the same also applies in reverse. This results in a system which is capable of being regenerated over a relatively long period of time.

Advantageous further developments and embodiments ensue from the remaining subclaims and from the exemplary embodiment which is described in principle below with the aid of the drawing.

DETAILED DESCRIPTION OF THE INVENTION

Figure 1:
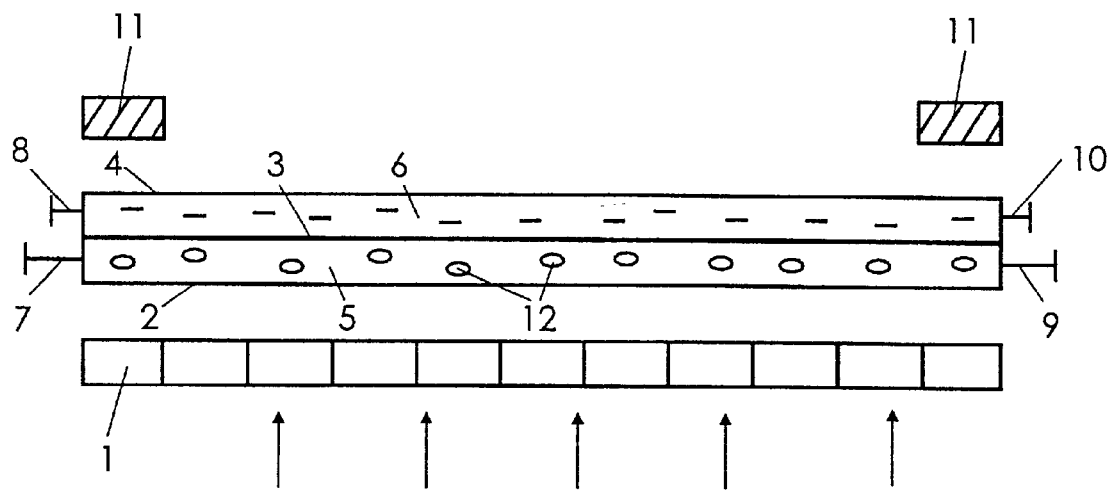
FIG. 1 shows an explosion diagram of the novel device in side view.

An elastic, gas-permeable Teflon membrane 2 is laid on a carrier 1 in the form of a carrier plate having a grid-like, apertured, profiled or honeycomb structure. A second film, in the form of a porous, liquid-permeable film 3, is laid over the Teflon film 2. A gas-permeable Teflon film 4 is laid over the film 3. The three films are sealed at their edges. In this way, a cell chamber 5, which is variable and which is capable of expanding freely upward, is formed between the Teflon film 2, which is supported continuously on the lower surface, and the second film 3, which is microporous, and a second chamber 6, which is variable and which is capable of expanding freely upward, is formed between the second film 3 and the third film 4. The second chamber 6 in each case possesses at least one supply line 7 or 8 and one discharge line 9 or 10. In order to achieve uniform distribution of substances which are to be introduced, and to achieve uniform flow-through, the supply and discharge lines for a chamber are arranged opposite each other, most suitably diagonally opposite. While one connection is in principle adequate for the cell chamber 5, it is possible to have several connections.

A frame, or several spacers 11, can be laid on the third film 4 as a cover and for position definition. The stable carrier 1, the cell chamber 5, the second chamber 6, which can serve as a nutrient medium chamber or collecting chamber, and the frame or the spacers 11, form a unit with it being possible to stack an arbitrary number of such units one above the other. Oxygen can be provided, from below through the carrier 1 in the direction of the arrow, and from the side between the spacers 11, for supplying cells 12 which have been introduced into the cell chamber 5. In the same way, nutrient medium can diffuse out of the second chamber 6, through the dialysis-like or microporous film 3, into the cell chamber 5.

Figure 2:
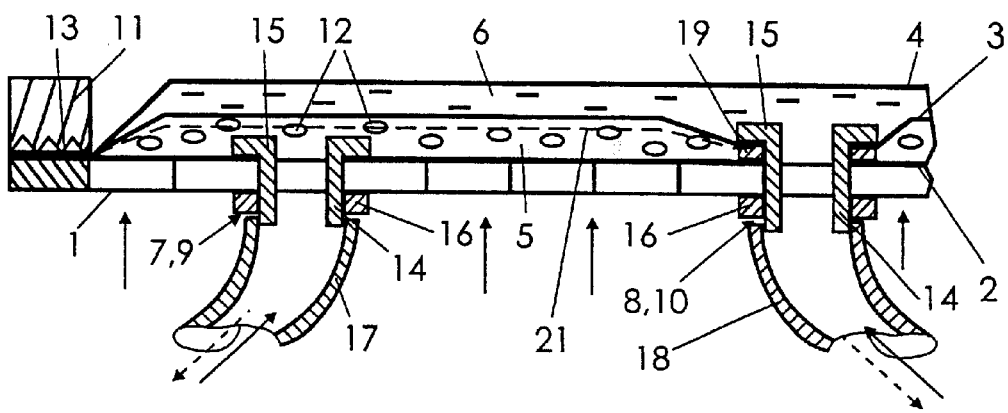
FIG. 2 shows a part of an enlarged representation, in vertical section.

FIG. 2 shows how the cell chamber 5 and the second chamber 6 are formed and how the films 2, 3 and 4 are sealed at their edges in order to form the two chambers. For this, the frame or the strip-like spacers 11 can be provided, on their underside, with a sawtooth-like structure 13 as a clamping or sealing member. The three films 2, 3 and 4 are laid on the carrier frame 1 and, after the spacer 11 has been put in place, are clamped by the sawtooth-like structure 13 when the spacers 11 are connected to the carrier 1 in a manner which is not depicted in detail. This can be effected, for example, using screw connections or by means of gluing. This results in all-round sealing.

The films 2, 3, 4 can also be glued or welded. However, the supply lines 7 and 8 and the discharge lines 9 and 10 have to be inserted before the frame or the spacer 11 is-put in place. The supply and discharge lines can be in the form of ready-made units. In order to create a connection to the outside, they can in each case possess a pipe part 14 having an annular head member 15. The pipe part 14 has an external thread onto which a thread nut 16 can be screwed. As soon as the Teflon film 2 has been put in place on the carrier 1, at least one supply line 7, having the pipe part 14, and one discharge line 9, likewise having the pipe part 14 of the same design, are in each case pushed through the membrane 2 and in each case inserted into a boring in the carrier 1. In association with this, the head member 15 fits closely on the upper side of the carrier 1 and the film 2 is clamped under it, with it being possible to provide a sealing ring (O ring) as well where appropriate. Sealing is achieved if the thread nut 16 is now screwed on from below. In conclusion, the hoses 17 and 18, respectively, can be slid onto the pipe part 14. In this way, the cell chamber 5 can be filled or emptied.

After the microporous film 3 has been put in place, the part pipe 14 is likewise pushed through it, which pipe part is then also inserted through a boring in the carrier 1. The pipe part 14 is either the supply line or the discharge line for the second chamber 6, provided there is no intention simply to have one common line for supply and discharge.

Advantageously, a sealing ring 19 is additionally provided between the head member 15 and the carrier 1. This arrangement likewise provides the possibility of supplying and discharging medium which is to be introduced into the second chamber.

At the beginning of the treatment, the three films 2, 3 and 4 lie directly on top of one another. If medium is now fed into the cell chamber 5, an appropriate, variable distance can be assumed, on account of the elasticity of the film 3 and, where appropriate, of the film 2 as well, thereby creating a corresponding treatment chamber or cell chamber 5. The same applies to the second chamber 6, which is likewise formed by a medium, e.g. nutrient medium, being introduced by way of the supply line 8. In this case, the film 4 is stretched, in addition to the film 3, and provides sufficient space for the second chamber 6 which is to be formed thereby. Since there are no particular restrictions in the upward direction, the volume in the cell chamber 5 and the second chamber 6 can expand upward as desired. Heights of from 1 to 2 cm can be achieved starting from a "zero distance".

If, for example, bone marrow is cultured in the cell chamber 5, it is possible to increase the volume by a factor of 100–1000. For example, the initial volume is from 100 microliters to 5 ml if only a thin film of cells 12 is present. The cells then grow in the cell chamber 5 by multiplication of the hematopoietic stem cells. Since growth factors are very expensive, this means that it is possible in the case of the novel device, to start with small quantities and in this way achieve a corresponding saving in costs. Despite this, it is not necessary to interrupt the treatment or to change the device since the system can, of course, grow in pace with the treatment. In addition, the construction principle makes it possible for bone marrow stroma cells to be able to remain in the bioreactor during multiplication of the stem cells.

The novel device can, for example, also be used for preparing antibodies or vaccines. In this case, immunoactivating viral or bacterial constituents are fed into the cell chamber 5; the clones which form in turn produce antibodies, which diffuse through the film 3 and can then be "harvested" from the second chamber 6 without causing any disturbance in the cell chamber 5. If required, the cell chamber 5 can also be subdivided as well.

It is readily possible to observe the events in the second chamber 6 and/or cell chamber 5 when using the novel device. Thus, the device can without difficulty be slid under a microscope without this having any effect on the cultures in the chambers. In practice, it is possible to observe every individual unit, or every module in this way.

Instead of films 2, 3 and 4 being clamped, as depicted in FIG. 2, they can also be glued onto the carrier 1 at the sides or all round.

Depending on the cell type and/or the form of culture, it is also possible, where appropriate, to manage with only one single chamber, in this case cell chamber 5, and with only two films, namely films 2 and 3. Thus, it is possible, for example, to culture fungi in cell chamber 5, which fungi are able to grow with a corresponding increase in the volume of cell chamber 5 due to the elasticity of film 3 and, where appropriate, of film 2 as well.

It is also possible to use an intermediate film 21 (shown in FIG. 2 as a broken line in cell chamber 5), resulting in two cell chamber sections being formed. The second film 11 can if necessary also be microporous.

One of the important advantages of the novel device is that, as a result of the concomitant growth of cell chamber 5 and the second chamber 6, there is no need, when harvesting substances from the second chamber 6, for the cells in cell chamber 5 to have to suffer from this, or to have to be removed at the same time, and thereby be lost, as in the state of the art.

This means, for example, that, when bone marrow is being expanded, the hematopoietic stem cells are able to expand and, at the same time, the stroma cells are able to remain in the bioreactor over long periods, i.e. until the stem cells have reached a satisfactory increase in volume, e.g. 500 ml from 1 to 5 ml).

It is furthermore also advantageous that at least the carrier 1 and the frame or the spacer 11 of the unit can be reused after an experimental series has come to an end. It is only necessary to replace the two chambers, namely cell chamber 5 and the second chamber 6, which chambers are formed from films 2, 3 and 4 and in practice constitute pouches. The supply and discharge lines 7 to 10 can also be reused.

Because of the low availability of particular starter cells (e.g. human bone marrow) and/or the enormous cost of growth factors and interleukins, the volume should be as small as possible (from approx. 1 to 5 ml); on the other hand, however, this volume should be able to increase up to 100 to 1000 times during the culture. Thus, a bone marrow from a patient, for example, should be multiplied extracorporeally such that approx. 500 ml can be transplanted back again.

In addition, specific culture phases may, e.g. in the case of liver cells, require large volumes (from 200 to 300 ml, in the case of a 1000 $cm^2$ surface area) of nutrient medium to be introduced into the bioreactor, which is created by the novel device, in order to enable the cells to grow optimally, and for a multiplication phase to take place over the subsequent 24 or 48 hours, without maintenance and under non-perfused conditions. It is precisely when cells are in the growth phase that it is necessary to avoid any disturbing flows. However, if the volume of a bioreactor were already initially set to very low volumes, this would mean that the tolerance time was very much reduced when the perfusion stopped since the nutrient medium would be consumed within minutes. In addition, toxic products from cells, catabolites, and also cell lysis products which accumulate when using collagenase to isolate cells in the cell isolation of primary cells (e.g. liver), would, at high local concentrations, impede the growth, and consequently the start of the culture and lead to the death of sensitive cells.

The following procedure is adopted when preparing to culture primary liver cells:

First of all, a liquid solution of collagen, e.g. 1.5 mg of type I collagen/ml and 3 µg of fibronectin/ml in 1 mmol HCl, is injected into cell chamber 5 or the cell compartment, and excess collagen is then immediately removed once again. This collapses the reactor in a bubble-free manner, since a vacuum is drawn, without any additional opening of valves. This flexibility is consequently also advantageous from the point of view of sterility and culturing, since air bubbles are toxic for cells. The removal of the excess collagen also represents a cost saving since this collagen can thereby also be used for other modules.

The reactor or the device can in this way be left at 37° C, or be irradiated with UV light, in order to bond (crosslink) the collagen. The collagen can be added to cell chamber 5 with or without a 10-fold concentrate of a nutrient medium, thereby enabling the pH to be neutralized immediately. If this is not done, for the sake of simplicity, the flexibility of the device then still allows the pH to be neutralized by adding a high proportion of nutrient medium, since the dilution effect of the culture medium enables the requisite buffering to be achieved.

The concentration is normally adjusted to $1 \times 10^6$ cells per ml when sowing hepatocytes. 200 ml would therefore be required for a culture surface area of 1000 $cm^2$. This volume is replaced after a period of from 2 to 4 h in order to remove toxins and cell detritus and to be able to leave fresh nutrient medium on the hepatocytes for a further 24 to 48 hours. After that, the medium is removed completely such that only a single, not yet confluent cell layer remains. This cell layer is then overlaid with from approx. 20 to 50 ml of collagen mixed, in cell chamber 5, with a 10-fold concentrate of a nutrient medium (e.g. Williams E). After that, excess collagen is once again sucked out of cell chamber 5. This enables cell chamber 5 to collapse and the lower gas-permeable film or membrane 2, together with the cells which have grown on it, to approach the central film 3 or membrane. This provides support for the firmness of the collagen layer and protects from shearing force effects.

After having introduced the second collagen layer into cell chamber 5 (48 h after sowing cells), and then having waited for approx. 1 h, the upper, second chamber is then filled with nutrient medium.

The higher the volume of nutrient medium, the easier it is for the bioreactor to be held in stand-by mode.

When primary hepatocytes are used, it is advantageous, contrary to the established view, to admix a proportion of not less than 1% (from 20 to 30%) of nonparenchymal cells into the culture since these cells produce growth factors locally and as a result enable the hepatocytes, which are not otherwise proliferating, to expand spontaneously. Otherwise, the hepatocytes would have had to be stimulated with high quantities of exogenously supplied, and very expensive, growth factors (e.g. EGF=epidermal growth factor, TGF=transforming growth factor or HGF=hepatocyte growth factor). The secretion of the endogenously produced cells (by the NPC=nonparenchymal cells) can be further augmented with GH=growth hormone, and cellular regeneration of the bioreactor thereby achieved inexpensively during relatively long-term operation.

If the reactor system is to be used as a bioartificial organ (e.g. liver), a minimal volume is then required, since substance exchange by diffusion is substantially more efficient when the thicknesses of the plasma layers employed are reduced and because products of the reactor are not then diluted down to unphysiological concentrations. In this connection, the vertical height of the perfusion chamber or second chamber 6 should then only be from 10 to 50 μm.

In order to be able to use them in vivo for patients suffering from liver failure, the bioreactor modules are connected in parallel using sterile connectors, the culture medium is removed completely by aspiration through multichannel pump systems, and the patient plasma (in combination with a plasma separator and a reservoir) is conducted through the upper second chamber 6 in layers which are as thin as possible. For this, it is once again advantageous for suction to be used for conducting the plasma through the reactor or the device since the latter can then collapse to the minimal volume. In order to provide support and safety during the perfusion operation, an in-line pump located upstream of the reactor can then make it possible to maintain constant perfusion conditions during reactor operation in association with minimal layer thicknesses.

The device can also be used for culturing keratinocytes on gas-permeable films such as Teflon. These films have high oxygen permeability when their layer thicknesses are low (e.g. 25 μm). When keratinocytes are expanded on films, as is customarily the case, the problem has previously has arisen that, when these films are used as wound coverings (e.g. after burns and removal of the burnt tissue remnants by escharectomy), the cells which have grown on the films are incorrectly orientated after the film has been turned over on the wound since keratinization always takes place on a side which is exposed to the air.

When the gas-permeable film 2 is used as the adhesion substrate, the keratinocytes initially adhere and proliferate; multilayer growth can also occur, as is usual. If the thickness of the medium layer overlying the cells in the second chamber 6 is increased during culture to the extent that limitations arise with regard to the $O_2$ supply, the cells can then reorientate, with keratinization being present on their lower sides. The $O_2$ supply depends on the thickness of the medium layer in accordance with Fick's law of diffusion, and $O_2$ tends towards 0 pericellularly at layer thicknesses of 1 mm.

If the bioreactor on this side, or the film 2, is then designed for this use such that the film 2 can be pulled off, in the shape of a cup, at predetermined breakage sites or earmarked detachment surfaces (non-permanent attachment), then this very simply makes it possible to achieve a sterile wound covering with correctly oriented, multilayer keratinocyte cultures.

For this purpose, the bioreactor can, for reasons of sterility, have an additional and removable sterile housing (case or additional film, gas-permeable membranes or structure, paper packaging or synthetic material having sterile filters which let air into the device).

This variability in the bioreactor, i.e. the ability to enable high and very low volumes to be achieved in a chronologically staggered manner, is an important advantage of the invention. This flexibility also makes it possible to culture organ and cell systems which differ in this way and to expand these systems in multicellular and multilayer cultures.

In this connection, the construction principle is consequently a volume-sensitive construction principle which makes possible a method in which different volumes can be set in a chronologically fractionated manner. This also means that the reactor "grows concomitantly" and, contrary to the state of the art, does not have any unwanted "dead volume".

When culturing the cells in the lower cell chamber 5, or the compartment, and with the close proximity to the oxygen supply which results therefrom, it is not absolutely necessary for the upper film 4 to be gas-permeable. In general, cell chamber 5 is arranged on the carrier 1. However, the reverse arrangement, i.e. with cell chamber 5 being located above and the second chamber being located below, is also possible, where appropriate, with the second chamber 6 in this case resting on the carrier 1 for support.

Figure 3:
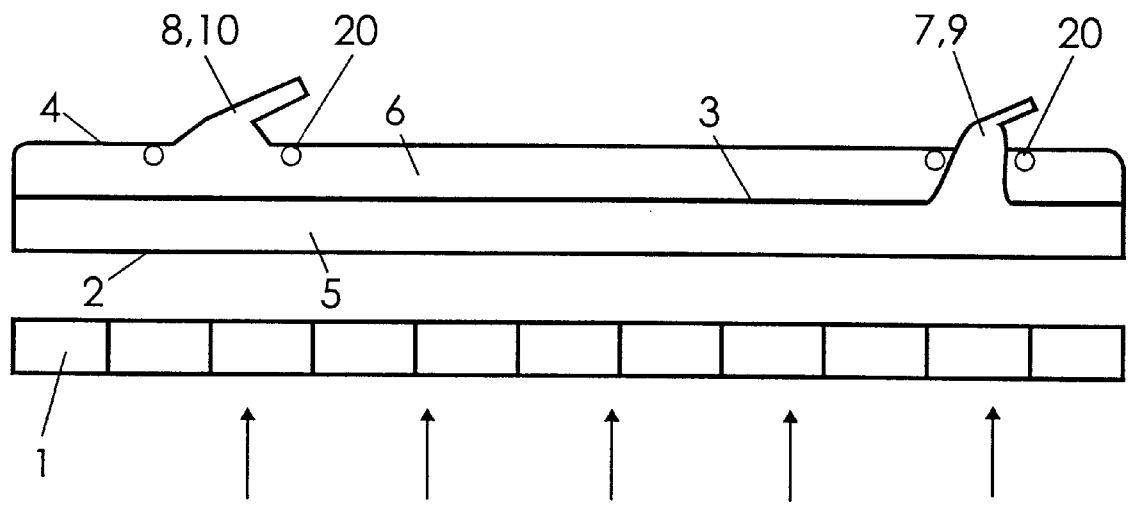
FIG. 3 shows a diagram of a modification of the novel device.
Figure 4:
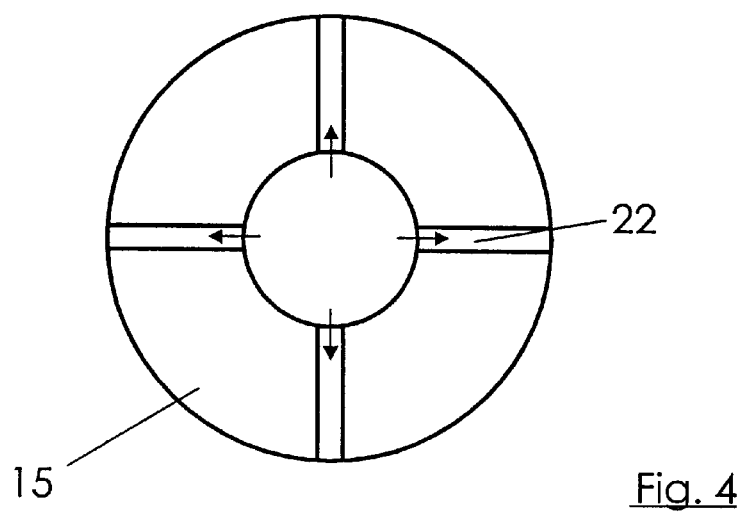
FIG. 4 shows a plan view of an enlarged representation of a head member of a pipe part of a supply or discharge line.

For the sake of simplicity, the connections or supply and discharge lines 7 to 10 can all be led out either at the top or at the bottom (or led out in a mixed manner). The advantage of attaching at the top is that the lines can be integrated right away into the upper film 4 or 3 during manufacture (e.g. deep-draw process) (see diagram in FIG. 3). FIG. 3 also shows that spacers 20 or distancing knobs are provided for the purpose of preventing the films 2, 3 and 4 from attaching themselves to each other by suction, or adhering to each other, in the region of the supply and discharge lines 7 to 10. Attachment to each other by adhering or sucking can also be prevented by, for example, channels which lead radially outward being formed in the head members 15 of the pipe parts 14 of the supply and return openings, thereby ensuring that medium can be introduced into the relevant chamber even when the films are lying directly on top of each other or are attached to each other by suction.

The bioreactor or the device can also be constructed such that the culturing unit is built as a pouch using the films 2, 3, 4 and the corresponding connections, in addition to chambers 5 and 6 which are formed therefrom. The bioreactor or the culturing unit can then be placed on the supporting carrier 1 and fixed to it. This can be effected by clamping using lateral holes in the pouch.

The bioreactor would not function correctly using the pouch on its own since the requisite flexibility and simple handling are only achieved in combination with a supporting structure or the carrier 1. Filling the pouch without the continuous supporting structure or the carrier 1 would immediately lead to the media or the cells dropping down to the lowest point and consequently to the cells dying off.

Ideally, the pore size of film 3 is 0.2 μm (sterile filtration limit), thereby additionally making it possible to provide cell chamber 5 with sterile protection. However, it is also possible to use larger or smaller pore sizes. These pore sizes can be selected such that they are so small that, for example, viruses, which are used for transfection experiments, on, for example, hepatocytes or bone marrow cells or keratinocytes, are retained in the appropriate cell chamber 5.

Examples of film materials which can be used are Teflon, silicone, polycarbonate or polyester. Polycarbonate or polyester is, in particular, suitable for the microporous film 3 on account of its transparency.

The surfaces of the films and hoses can, for example, be precoated with heparin so as to reduce complement activation.

In contrast to hollow fiber systems, it is very easily possible to remove the cells, which are growing as layers, after, for example, detaching them by trypsinization as well, or by simply aspirating.

The novel device can also be used for dealing with plant cells or algae, which can carry out photosynthesis in the transparent bioreactors for the purpose of producing oxygen, for example. This could be of use in space travel, for example, for absorbing $CO_2$ and providing $O_2$.

Furthermore, such systems could be employed when using bacteria for detoxifying atmospheres which have been contaminated with gases.

What is claimed is:

1. Device for culturing and/or treating cells, the device comprising:
   a first cell chamber arranged on a gas-permeable carrier;
   the first cell chamber is formed by a first film, said first film being a gas-permeable, non-liquid-permeable film which is laid on the carrier, and a second film, said second film being a microporous film, which is arranged over the first film or is integral with the first film;
   at least one of the two films is elastic such that a final volume of the first cell chamber can be at least 100 times its starting volume; and
   the first cell chamber is provided with at least one supply and/or discharge line, and a frame to cover the films.

2. Device according to claim 1, further having a third film arranged over the second film and connected to the second film or is integral with the second film, with the second film and/or the third film being elastic such that a second cell chamber is formed between the second film and the third film, the final volume of which chamber can be at least 100 times its starting volume, with the second film being a microporous film which permits the passage of selected substances from the first cell chamber into the second cell chamber, with the second cell chamber being provided with at least one supply and/or discharge line.

3. Device according to claim 2, wherein a multiplicity of first cell chambers which are formed from first and second films and second cell chambers which are formed from second and third films are laid one above the other by frames placed over the third film.

4. Device according to claim 1, wherein the frame placed over the films forms a unit such that multiple units may be stacked one above the other.

5. Device according to claim 4, wherein the frame is provided, on its underside, with clamping and/or sealing members for the films.

6. Device according to claim 2, wherein the films are connected, at their edges and in a liquid-tight manner, to the carrier and/or to each other.

7. Device according to claim 6, wherein the films are glued to the carrier.

8. Device according to claim 2, wherein the supply and discharge lines are prefabricated units which are inserted through the respective pertinent film and affixed thereto, and can be affixed to the carrier.

9. Device according to claim 8, wherein the prefabricated units can be connected to the carrier by means of holding connections.

10. Device according to claim 8, wherein each prefabricated unit possesses a pipe part having a thread section onto which a thread nut can be screwed, with the carrier being clamped between a head member of the pipe part and the thread nut.

11. Device according to claim 10, wherein sealing rings or spacers are arranged between the head member and the carrier and/or a film.

12. Device according to claim 2, wherein the films consist of Teflon, silicone, polycarbonate or polyester.

13. Device according to claim 1, wherein the carrier is in the form of a gridded or hole-profiled plate.

14. Device according to claim 2, wherein the supply and discharge lines are integrated as a unit into the third film and the second film.

15. Device according to claim 1, wherein the first cell chamber is subdivided into two sections by means of an intermediate film.

16. Process for culturing and/or treating cells in the following steps:
   a first gas-permeable, non-liquid-permeable film is laid on a gas-permeable carrier;
   a second microporous film is laid on the first film, with at least one of the two films being elastic, thereby forming a first cell chamber that allows a variable volume of at least 100 times for said first cell chamber;
   a third film is laid on the second film, with the second or the third film being elastic such that a second cell chamber allowing a variable volume of at least 100 times is formed therebetween;
   the films are sealed at their edges;
   cells are introduced, for culturing and/or treatment, in said first cell chamber between the first film and the second film; and
   a second medium is introduced in said second cell chamber between the second and third film.

* * * * *